July 12, 1960 W. LEE Plant Pat. 1,959
PYRACANTHA PLANT
Filed Dec. 19, 1958 2 Sheets-Sheet 1
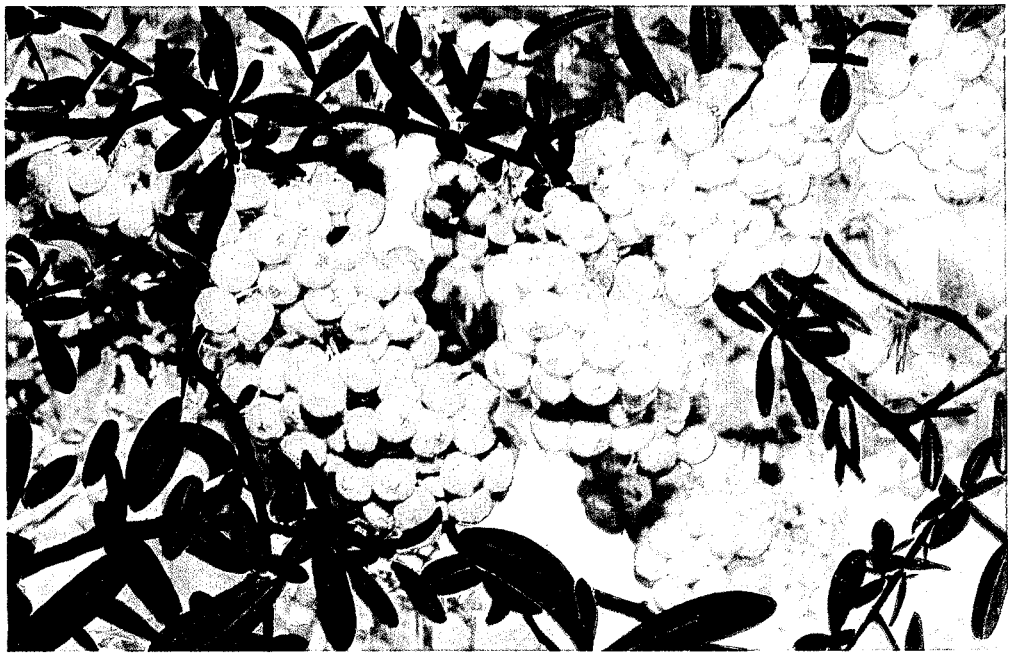
INVENTOR.
WALTER LEE
BY J. F. Cuneo
ATTORNEY PYRACANTHA PLANT
Filed Dec. 19, 1958 2 Sheets-Sheet 2
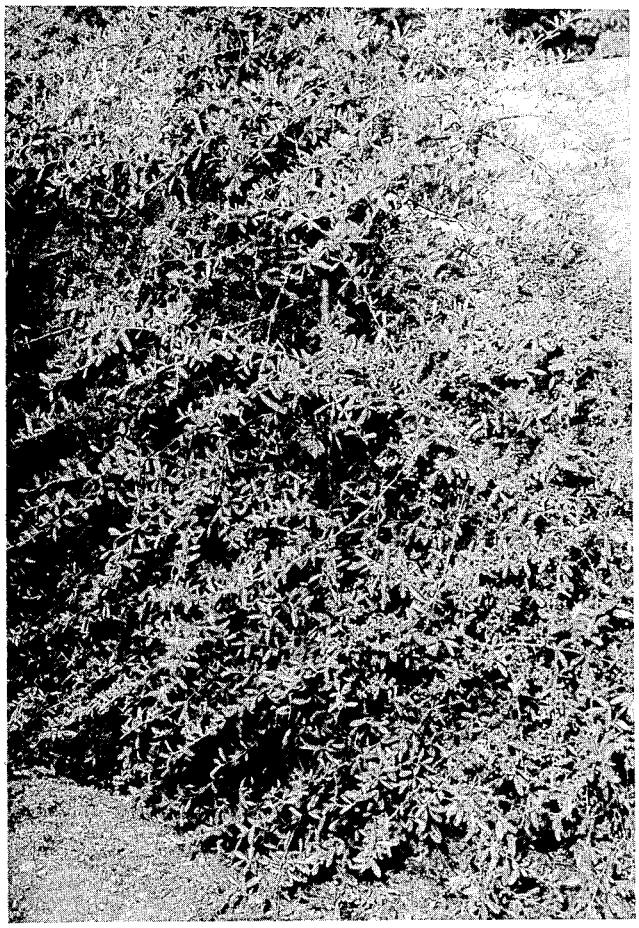
INVENTOR
WALTER LEE
BY J. F. Cuneo
ATTORNEY United States Patent Office Plant Pat. 1,959
Patented July 12, 1960

1,959

PYRACANTHA PLANT

Walter Lee, Bellflower, Calif., assignor to Monrovia Nursery Co., Azusa, Calif., a corporation of California Filed Dec. 19, 1958, Ser. No. 781,821

1 Claim. (Cl. 47—59)

This invention relates to a new and distinct variety of Pyracantha plant having especially attractive features as an ornamental shrub, and in particular to a new plant of this type characterized by its upright compact growth, and the abundance of bright red berries that can withstand cold weather without losing their red color. Other varieties of Pyracantha plants have berries that are either not as bright a red as those of the plant according to this invention, or if they are red during mild weather, they become a light orange when exposed to cold weather.

The fact that the plant has an abundance of bright red berries, that closely resemble holly berries in color and appearance, makes the plant a particularly attractive addition to any garden during the winter, and especially during the holiday season since it adds considerable color to an otherwise drab landscape.

The plant resulted by cross-breeding *Pyracantha crenata-serrata* Rosedale, an unpatented variety, with *Pyracantha coccinea lalandi*, also an unpatented variety, after numerous experiments conducted by me in southern California, in the coastal foothill area of Los Angeles County. The original plant was produced by me in July of 1949; by cross-breeding the above named species I have developed a new variety that differs from its parent plant *Pyracantha crenata-serrata* Rosedale in that the plant is more resistant to cold, the fruit or berries are a brighter red and are larger in size, being borne by the plant in clusters which are evenly produced on the plant's previous year's growth of wood as well as on the older wood, and the leaves are longer. The plant did not suffer when exposed to temperature of 19° F. at the growing grounds in southern California and the berries retained their pure red color. A particular distinction between the plants is that the berries of the new variety remain a bright red when exposed to cold weather, whereas, those of the parent plant turn a dull red. The new variety differs from its other parent plant, *Pyracantha coccinea lalandi* in that it has a more compact growth habit, its berries are bright red, its leaves are narrower and longer, and the berries of the parent plant turn light orange when subjected to cold weather. *Pyracantha coccinea lalandi* also is different from the novel variety in that the parent plant is semi prostrate where the new species is upright. The new species of Pyracantha was especially developed to make available a plant that would produce bright red berries and yet be capable of withstanding cold weather. There is no known variety of Pyracantha on the market which has true red berries that will retain their bright red coloring when the plant is subjected to temperatures substantially below 19° F., and many varieties lose their coloring before reaching 19° F. Some of the plants according to this invention were tested in New Jersey where the temperature reached 5° to 6° above zero during December of 1958, and January of 1959. This winter was unusually severe and proved to be a very difficult year for all broadleaf material. Tests in this area showed that the berries produced by the new species appeared to keep their color and remain on long after those produced by *Pyracantha lalandi*, located in the same area, had dropped off.

The accompanying illustrations show a portion of the plant in color, including branches with thorns, leaves and clusters of berries at the time of maturity, and in black and white the upright, compact growth thereof.

This new variety of Pyracantha has been reproduced asexually by me in the growing grounds at Monrovia and Azusa, California, by means of cuttings, and the distinguishing characteristics are evident in the resulting plants and appear to be well established. The new variety cannot be reproduced by sexual means since the plant does not reproduce true from seed.

In the following description of the plant, bloom and berries, the color names and numbers that are used in describing the leaves and berries are based on the Horticultural Colour Chart designations adopted by the British Colour Council.

*The plant*

Form: A vigorous, compact, semi-upright growing shrub which has the habit of developing a central stock with alternate horizontal laterals.

Foliage: Heavy.

*Size.*—Most leaves are about 1½″ long and are about ½″ in width at the widest portion of the leaf.

*Color.*—Upper surface of the leaves is Spinach Green No. 0960, while the underside of the leaves is Scheeles Green, No. 860.

*Shape.*—The leaves are faintly serrate linear. Base of leaves is cuneate and the apex of the leaves is mucronate.

*Veins.*—The veins are not prominent on the underside and are a little more prominent on the upper side. The arrangement of the veins is alternate.

*Arrangement.*—The leaves are alternate and are attached to their respective stems by a short peduncle.

Stems: The stems of the plant are medium slender.

*Color.*—The stems vary from grey to greyish brown.

*Growth.*—Most stems are quite long.

Thorns: The thorns are long and needlelike and when fully developed are about 9/16″ long.

*Color.*—The thorns are usually reddish brown, becoming slightly darker at the ends.

*Arrangement.*—The thorns are essentially on the laterals and are spaced at random. These thorns extend outwardly at an angle to the stem.

*The bloom*

The plant blooms in the latter part of March and in April in southern California, where the climate varies considerably from year to year.

Arrangement: The blooms are borne in profusion and form in terminal clusters on the laterals.

Buds: The buds are attached to short peduncles in groups of three to four and vary in size from 1/16″ to ⅛″ in diameter. Several groups are usually clustered together and each cluster will usually include about twenty-one buds.

Flowers:

*Arrangement.*—The flowers are formed in corymbs which vary from 1¼″ to 2″ in diameter.

*Calyx.*—The color of the calyx is light green and varies from 1/16″ to ⅛″ in size.

*Petals.*—Style and number: The petals are arranged in groups of five and form a five pointed star. Size: The petals are from 1/16" to 1/8" in length and in the five pointed star arrangement are about 3/8" across. Color: The petals are white.

*Stamens.*—There are from 15 to 18 stamens in the flower. Color.—lemon yellow.

*Berries*

Texture: Pithy and dry.

Size: The berries vary between 5/16" and 3/8" in diameter.

Shape: Flattened globes at the opposite ends, having a star-shaped center.

Color: The berries are Oriental Red No. 819.

Arrangement: Attached to stems either singly or in clusters of two or three. Stems are short, light in weight and are usually light green.

Persistence: The berries remain on the bush throughout the winter and their bright red coloration persists even in very cold weather.

Ripening period: The berries begin to ripen in September but do not turn a vivid red until colder weather sets in.

Having described my invention, I claim:

The new and distinct variety of Pyracantha plant, substantially as herein shown and described, characterized especially by its upright compact growth, its abundance of bright red berries, and the ability of the berries to retain their bright red coloration after exposure to cold weather.

No references cited.